(12) United States Patent
Moser et al.

(10) Patent No.: US 8,660,656 B2
(45) Date of Patent: Feb. 25, 2014

(54) CUFF ASSEMBLY (75) Inventors: Joseph P. Moser, Wheaton, IL (US);
David Nieves, Port Jefferson, NY (US);
Mary-Kate Ennis, Austin, TX (US)

(73) Assignee: Hanger, Inc., Austin, TX (US)

( * ) Notice: Subject to any disclaimer, the term of this patent is extended or adjusted under 35 U.S.C. 154(b) by 181 days.

(21) Appl. No.: 12/581,059

(22) Filed: Oct. 16, 2009

(65) Prior Publication Data
US 2011/0093035 A1    Apr. 21, 2011

(51) Int. Cl.
*A61N 1/18* (2006.01)

(52) U.S. Cl.
USPC .................................. 607/48; 607/46; 607/47

(58) Field of Classification Search
USPC ..................................................... 607/46–48
See application file for complete search history.

(56) References Cited

U.S. PATENT DOCUMENTS

| | | | |
|---|---|---|---|
| 3,955,560 | A | 5/1976 | Stein et al. |
| 4,428,369 | A | 1/1984 | Peckham et al. |
| 5,052,379 | A | 10/1991 | Airy et al. |
| 5,330,516 | A | 7/1994 | Nathan |
| 5,554,104 | A | 9/1996 | Grim |
| 5,562,707 | A | 10/1996 | Prochazka et al. |
| 5,643,332 | A | 7/1997 | Stein |
| 5,725,489 | A | 3/1998 | Bar-Or et al. |
| 5,782,785 | A * | 7/1998 | Herzberg .................... 602/26 |
| 5,814,093 | A | 9/1998 | Stein |
| 5,833,716 | A | 11/1998 | Bar-Or et al. |
| 5,865,776 | A | 2/1999 | Springs |
| 6,829,510 | B2 | 12/2004 | Nathan et al. |
| 7,146,220 | B2 | 12/2006 | Dar et al. |
| 7,149,582 | B2 | 12/2006 | Dar et al. |
| 7,337,007 | B2 | 2/2008 | Nathan et al. |
| 7,632,239 | B2 | 12/2009 | Dar et al. |
| 2003/0114892 | A1 | 6/2003 | Nathan et al. |
| 2003/0114893 | A1 | 6/2003 | Nathan et al. |
| 2003/0114894 | A1 | 6/2003 | Dar et al. |
| 2005/0192645 | A1 | 9/2005 | Stein et al. |
| 2007/0112285 | A1 | 5/2007 | Dar et al. |
| 2007/0112394 | A1 | 5/2007 | Nathan et al. |
| 2007/0197946 | A1 | 8/2007 | Gilmour |
| 2008/0064996 | A1* | 3/2008 | Bretl et al. ...................... 602/21 |
| 2008/0288035 | A1 | 11/2008 | Gill et al. |
| 2009/0069865 | A1 | 3/2009 | Lasko et al. |
| 2009/0177131 | A1 | 7/2009 | Dar et al. |

FOREIGN PATENT DOCUMENTS

| | | |
|---|---|---|
| CA | 2232672 C | 8/2001 |
| WO | WO-98/53877 | 12/1998 |
| WO | WO-2009/098651 | 8/2009 |

OTHER PUBLICATIONS

International Search Report for International Application No. PCT/US2010/041764, mail date Feb. 28, 2011, 3 pages.
Foreign Search Report for EP 10823763.7, dated Dec. 10, 2013, 8 pages.

* cited by examiner

*Primary Examiner* — Joseph Stoklosa
(74) *Attorney, Agent, or Firm* — Foley & Lardner LLP (57) ABSTRACT

A cuff assembly includes a frame assembly configured to be positioned about a limb of a user and support a functional electrical stimulation system, and an over center closure mechanism coupled to the frame assembly and configured to secure the frame assembly relative to the limb, the over center closure mechanism being located on a medial side of the limb when the frame assembly is positioned about the limb.

16 Claims, 14 Drawing Sheets

CUFF ASSEMBLY

BACKGROUND

The present disclosure relates generally to the field of cuff assemblies. More specifically, the present disclosure relates to a cuff assembly that is attachable to a user's limb (e.g., leg, etc.) and is configured to support a control unit (e.g., a computerized control unit, etc.) that provides functional electrical stimulation (FES) to the neuromuscular system of the user.

FES systems are generally known and may be used to improve neuro-muscular functioning of users with various disabilities. However, there are many challenges associated with providing an effective FES system that is easy to use and adaptable to a wide variety of users.

SUMMARY

One embodiment relates to a cuff assembly comprising a frame assembly configured to be positioned about a limb of a user and support a functional electrical stimulation system, and an over center closure mechanism coupled to the frame assembly and configured to secure the frame assembly relative to the limb, the over center closure mechanism being located on a medial side of the limb when the frame assembly is positioned about the limb.

Another embodiment relates to a cuff assembly comprising a frame assembly having an at least partially flexible skeletal portion configured to extend about at least a portion of a circumference of a limb of a user, a strap assembly extending about at least a portion of the frame assembly and configured to support a control unit, and an over center closure mechanism coupled to at least one end of the strap assembly, the over center closure mechanism being moveable from an open position to a closed position to increase an amount of compressive force applied to the limb via the frame assembly.

Another embodiment relates to a cuff assembly comprising a frame assembly configured to extend about at least a portion of a limb of a user, a strap assembly configured to extend about at least a portion of the frame assembly, a first end of the strap assembly being coupled to the frame assembly, and a latch mechanism. The latch mechanism is located to a medial side of the limb and comprises a base coupled to the frame assembly, a first clip member coupled to a second end of the strap, and a second clip member coupled to the first clip member and having a first pin member configured to be rotatably received by a first portion of the base and a second pin member configured to be snap fit into a second portion of the base.

Another embodiment relates to a cuff assembly comprising one or more electrode locators that are configured to be removeably coupled to the interior of the cuff assembly and locate electrode assemblies relative to a limb of a user.

Another embodiment relates to a cuff assembly comprising an extra-skeletal frame member that includes an exposed exterior surface and is coupled to a liner assembly on an interior surface. The skeletal frame member may comprise a plurality of portions, each portion being molded using a separate molding process (e.g., injection molding, etc.), and each portion having a unique hardness relative to at least one other portion.

Yet another embodiment relates to a cuff assembly comprising a locating guide that is attached to a portion of the cuff assembly and is configured to be aligned with a tibial crest of a user when the cuff assembly is properly positioned on the user's leg.

BRIEF DESCRIPTION OF THE DRAWINGS

The present disclosure will become more fully understood from the following detailed description, taken in conjunction with the accompanying drawings, wherein like reference numerals refer to like elements.

DETAILED DESCRIPTION OF EXEMPLARY EMBODIMENTS

Various embodiments disclosed herein may be used in connection with one or more medical devices (e.g., neuro-prosthetic devices, etc.) intended to address neuro-muscular medical conditions in users of such devices. One such medical condition is drop foot, or foot drop, which is a disorder that can affect a person's ability to raise his or her foot at the ankle. Drop foot may also make walking a challenge, resulting in a person either dragging a foot and toes while walking, or having to walk with an unusually high step.

To address drop foot, a functional electrical stimulation (FES) system may be used to provide signals to nerves in the lower leg that then activate muscles to raise the foot at the appropriate time during walking, etc. A cuff assembly may be used to support the FES system, for example, by wrapping or extending about a lower leg portion of a user.

The cuff assembly described in the various embodiments disclosed herein may provide a variety of benefits to users, including enabling a user to don (e.g., put on) or doff (e.g., take off or remove) the cuff assembly utilizing only a single hand, minimizing the overall diameter and/or circumference of the cuff assembly to facilitate fitting pant legs or other clothing over the cuff assembly, and providing an easily repeatable locating of electrodes used by the FES system between wearings of the cuff to avoid having to repeatedly determine proper placement of electrodes via various calibration techniques. The cuff assembly may provide many other benefits to users as discussed in further detail below.

Referring now to FIGS. 1-5, a cuff or cuff assembly 10 (e.g., a support assembly, a neuro-prosthetic device or support, a brace, a wrap, etc.) is shown according to an exemplary embodiment. As shown in FIGS. 1-5, cuff 10 may include a frame assembly 12, a strap assembly 14, and a closure assembly shown as over center closure mechanism 18. Cuff 10 further includes one or more electrode locators 20, 22 that support and locate electrode assemblies 24, 26, which are in turn controlled by a control unit 16 (e.g., a computerized control unit, etc.) via wires 28, 30. Electrode locators 20, 22 may be coupled to a liner assembly 34 provided on an interior portion of frame assembly 12. A leg pad 38 may be provided between frame assembly 12 and strap assembly 14 to ensure a good fit of cuff assembly 10 and avoid discomfort to a user.

Cuff 10 is configured to support control unit 16 proximate a user's limb, such as a lower leg, so that electrode assemblies 24, 26 may provide proper stimulation to the nerves and/or muscles. A locating guide 36 may be provided as part of liner assembly 34 to provide a guide to properly locate cuff 10 about the circumference of a user's leg, such as limb 32 shown in FIGS. 3-4. According to an exemplary embodiment, locating guide 36 is positioned such that it aligns with the tibial crest of a user when cuff 10 is properly positioned on limb 32. This may facilitate proper positioning of cuff 10 over repeated uses.

Figure 16:
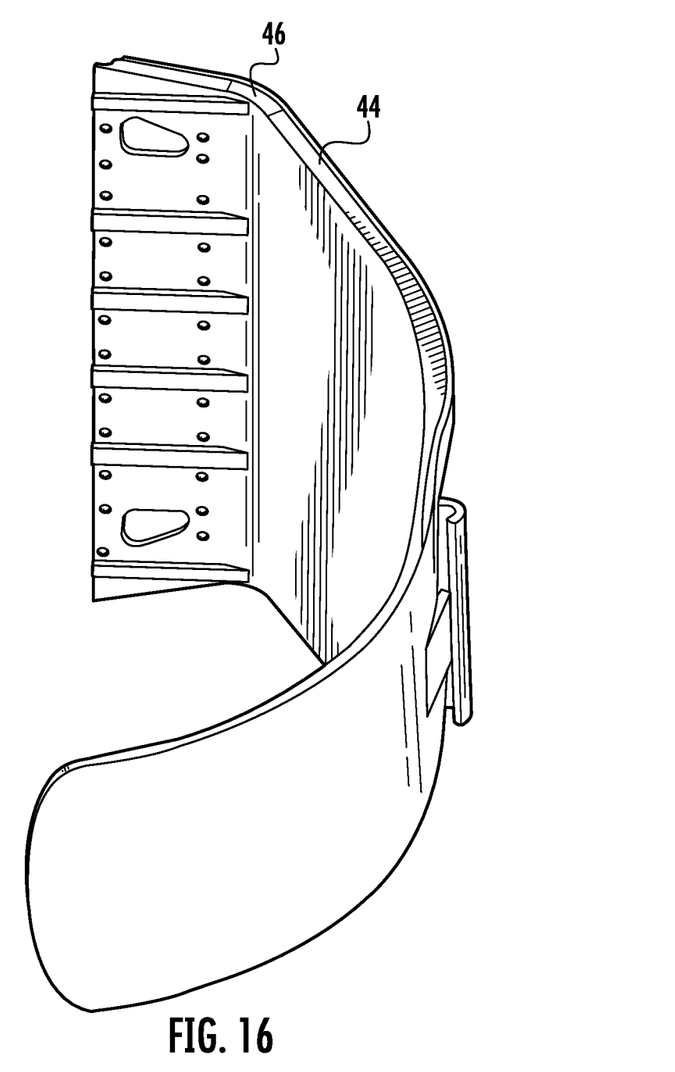
FIG. 16 is a perspective view of a portion of a skeleton member after a first molding process according to an exemplary embodiment.
Figure 17:
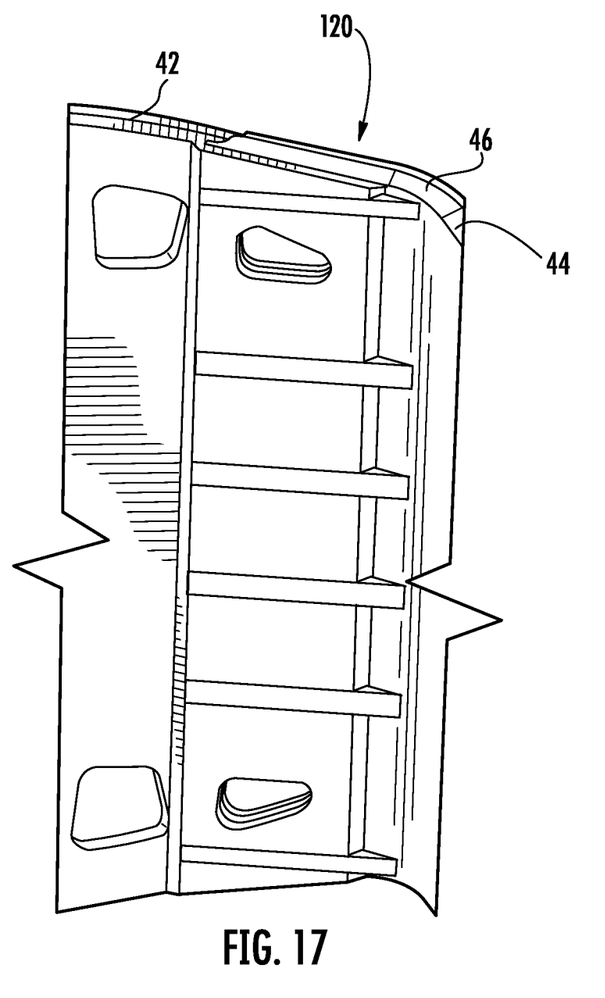
FIG. 17 is a perspective view of a portion of a skeleton member after a second molding process according to an exemplary embodiment.

Referring now to FIGS. 5-18, the various components of cuff assembly 10 will be described in greater detail. As shown in FIGS. 6-10, frame assembly 12 includes a skeleton member 40 (e.g., a frame, an exoskeleton, a molded member, an armature, etc.) and a liner assembly 34. Frame assembly 12 may be any suitable width (e.g., 2 inches, 4 inches, etc.). According to various exemplary embodiments, skeleton member 40 may be a rigid, semi-rigid, or flexible member made from a polymer material (e.g., High-Density Polyethylene (HDPE), Santoprene, a combination thereof, etc.) via one or more injection molding processes or another suitable molding, forming, or other manufacturing process. For example, as shown in FIG. 7, skeleton member may 40 comprise a first portion 42 and a second portion 44 made from differing materials having different characteristics (e.g., different colors, hardness, durometer values, flexibility, etc.). In one embodiment, second portion 44 is formed from HDPE (e.g., a rigid or semi-rigid material) utilizing a first injection molding process (see FIG. 16), and then first portion 42 is over-molded onto at least a portion of second portion 44 utilizing a Santoprene material (e.g., a flexible material) and a second injection molding process (see FIG. 17). The HDPE material would have a higher durometer value, and therefore second portion 44 would be more rigid, than first portion 42, which would have a relatively lower durometer value associated with the Santoprene material. First and second portions 42, 44 may overlap each other at an overlap area 120 shown in FIG. 17. Other materials may be used according to various other exemplary embodiments.

Figure 6:
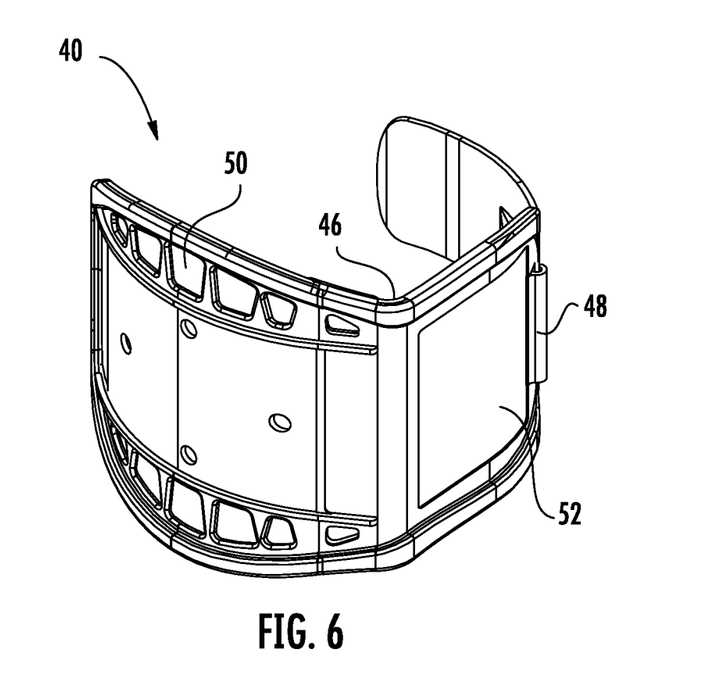
FIG. 6 is a perspective view of a skeleton member of a frame assembly according to an exemplary embodiment.
Figure 7:
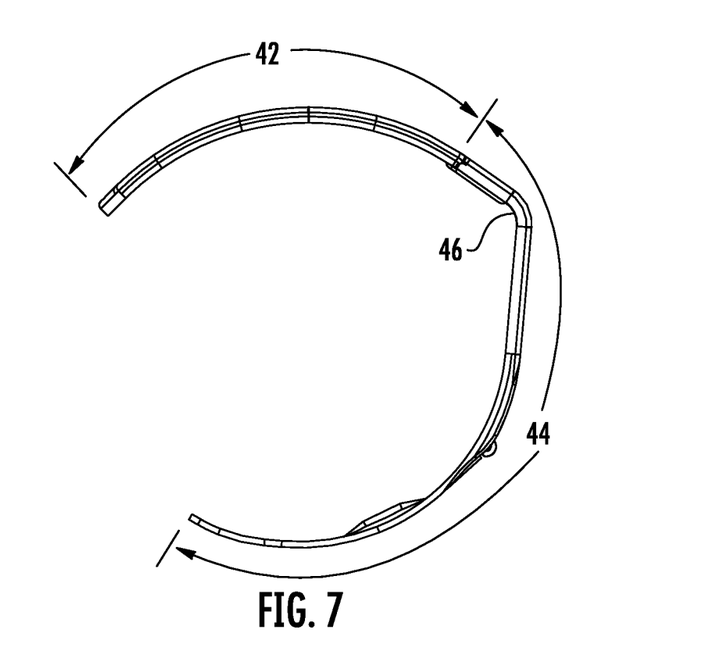
FIG. 7 is a top view of the skeleton member of FIG. 6 according to an exemplary embodiment.

As shown in FIGS. 6-7, skeleton member 40 may include one or more apertures 50 that may reduce the weight of skeleton member 40 without impairing the strength or structural characteristics of cuff 10. Further, skeleton member 40 includes an apex 46 (e.g., a curved portion, a groove, a corner, etc.) configured to conform to a tibial crest of a user. A flat portion or area 52 may be provided to a medial side of apex 46 and be sized to accommodate a side surface of control unit 16. A pin retainer 48 extends from one side of skeleton member 40 and in one embodiment is configured to retain a pin coupled to strap assembly 14, as discussed in greater detail below.

Figure 8:
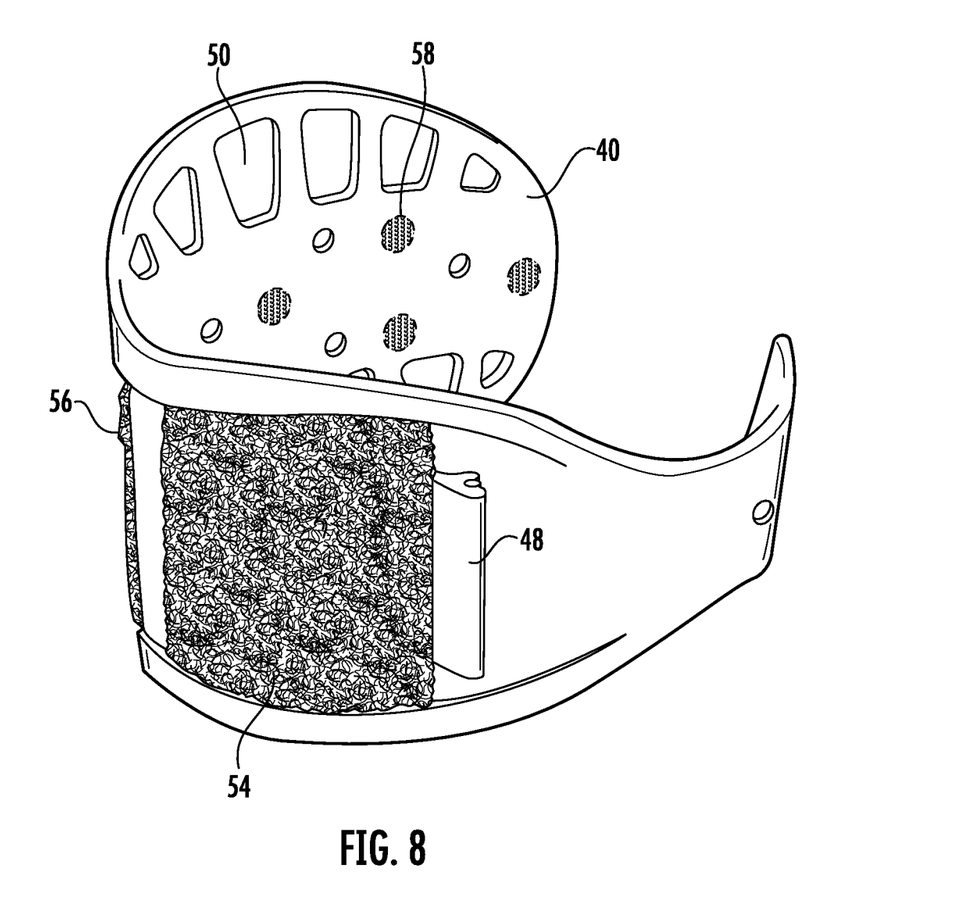
FIG. 8 is a perspective view of a skeleton assembly according to another exemplary embodiment.

Referring to FIG. 8, one or more pads 54, 56, 58 may be secured to skeleton member 40. For example, as shown in FIG. 8, pads 54, 56 may be located on an exterior or outward-facing surface of skeleton member 40, while one or more pads 58 may be located on an inward-facing or interior surface of skeleton member 40. In one embodiment, pads 54, 56, and 58 are secured to skeleton member 40 using an adhesive material. In a further embodiment, pads 54, 56, and 58 comprise outward-facing hook and/or loop material configured to enable coupling of additional components to frame assembly 12. In a yet further embodiment, pads 54, 56 comprise a loop material and pads 58 comprises a hook material.

Figure 5:
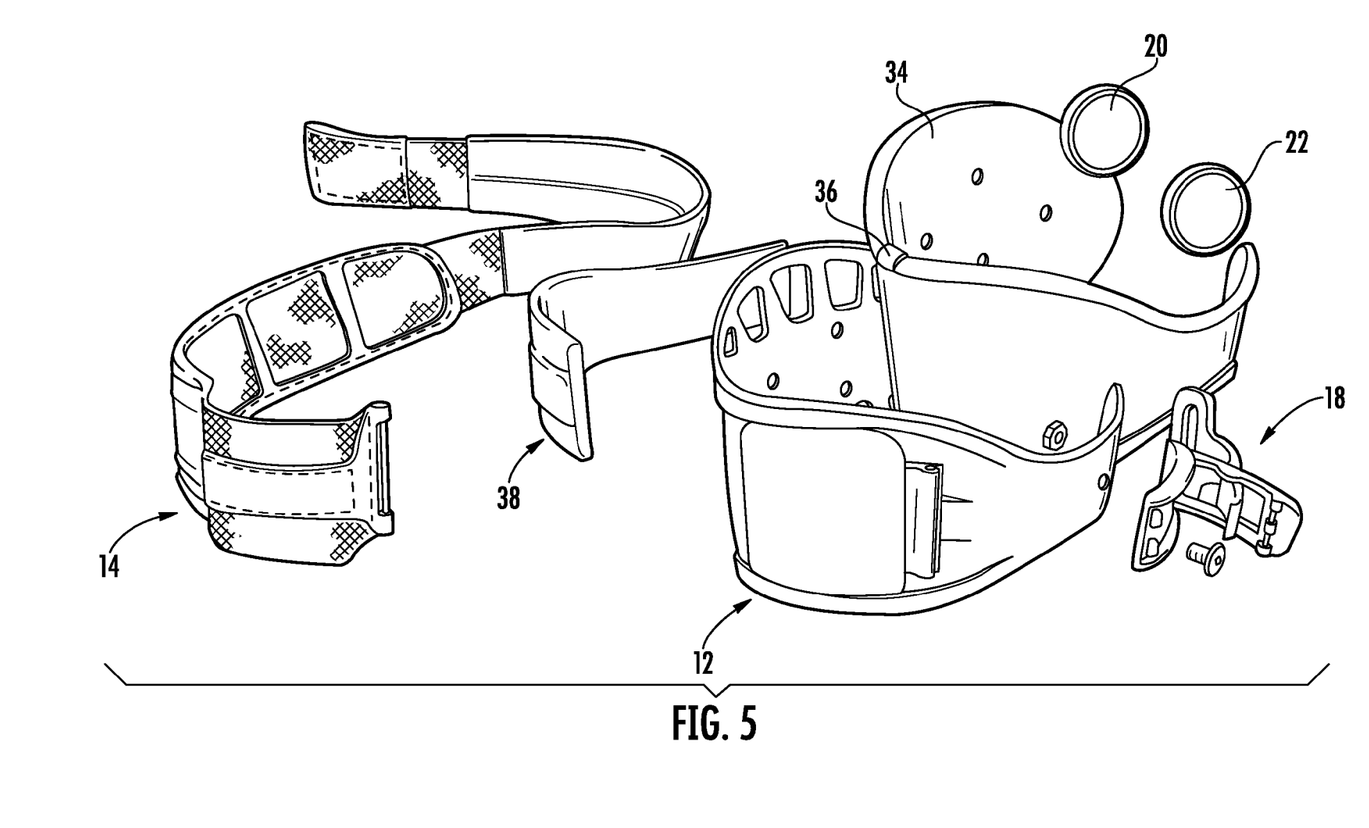
FIG. 5 is a an exploded view of a cuff assembly according to an exemplary embodiment.
Figure 9:
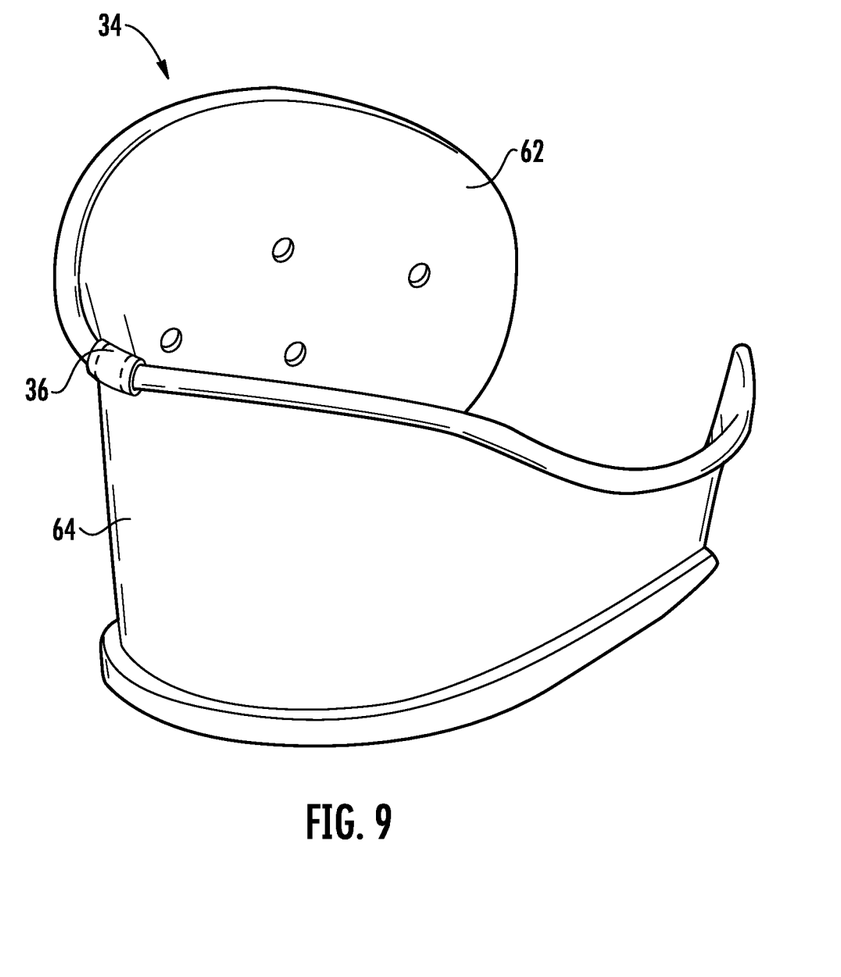
FIG. 9 is a perspective view of a liner assembly according to an exemplary embodiment.
Figure 10:
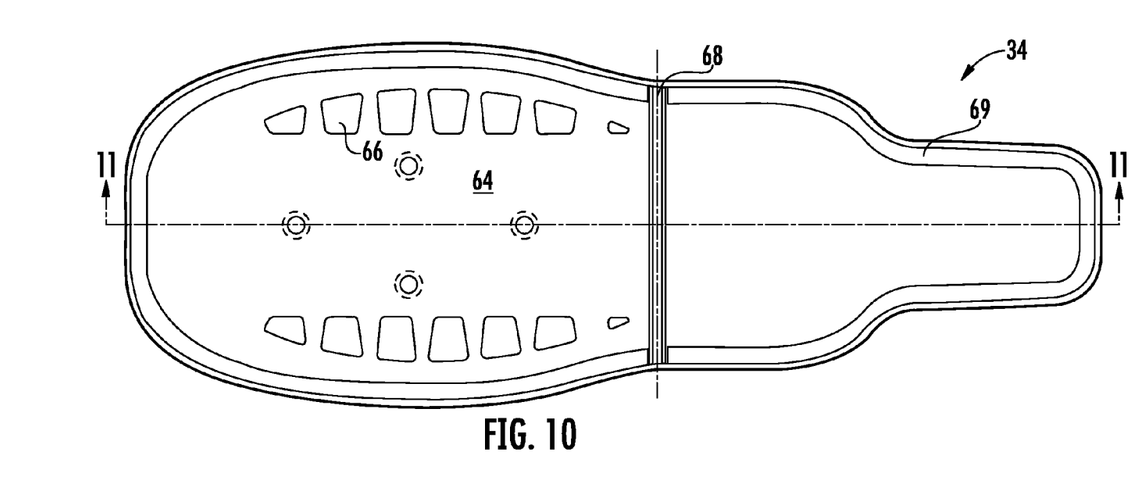
FIG. 10 is a plan view of a liner assembly according to an exemplary embodiment.
Figure 11:
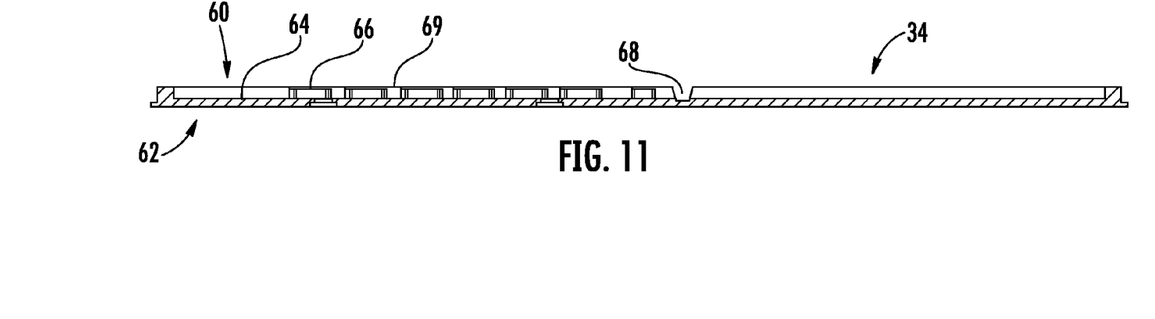
FIG. 11 is a cross sectional view of the liner assembly shown in FIG. 10 taken along line A-A of FIG. 10 according to an exemplary embodiment.

Referring now to FIGS. 9-11, liner assembly 34 is shown in greater detail according to an exemplary embodiment. Liner assembly 34 may be coupled to the inner surface of skeleton member 40, as shown in FIG. 5. In one embodiment, outer surface 60 of liner assembly 34 may comprise a hook and/or loop fastener material configured to couple with the hook and/or loop material provided on pads 58 of skeleton member 40. Inner surface 62 may similarly be provided with a hook and/or loop material to facilitate the locating and retention of electrode locators 20, 22 (see, e.g., FIG. 2) on inner surface 62. Other means (e.g., adhesives, mechanical fasteners, snap fit devices, etc.) may be used to secure liner assembly 34 to skeleton member 40 and/or electrode locators 20, 22 according to various alternative embodiments.

In one embodiment, locating guide 36 is located along a top edge of liner assembly 34 such that locating guide 36 aligns with the tibial crest of a lower leg when cuff assembly 10 is properly fitted to a user. In one embodiment, locating guide 36 is a piece of material that is sewn, adhered, or otherwise coupled to the main body of liner assembly 34. In further embodiments, locating guide 36 may be provided in a contrasting color (e.g., an orange color, etc.) from liner assembly 34 and/or other components of cuff 10 so as to be easily identifiable by a user. According to various other embodiments, locating guide 36 may comprise other features such as a notch, a printed marking, etc.

Referring to FIGS. 10-11, according to one embodiment, liner assembly 34 may be compression molded and include one or more raised portions 66, 69, and one or more lower or recessed portions 64. Portions 64, 66, 69 may be formed such that when liner assembly 34 is coupled to skeleton member 40, raised portions 66 extend at least partially through apertures 50 in skeleton member 40 and raised portion 69 extends about a portion or all of the perimeter of skeleton member 40. Liner assembly 34 may also include a groove or notch 68 located to align with the tibial crest of a lower leg of a user. In some embodiments, skeleton member 40 may be molded with a corresponding raised portion which may be received within notch 68 when liner assembly 34 is coupled to skeleton member 40.

Figure 1:
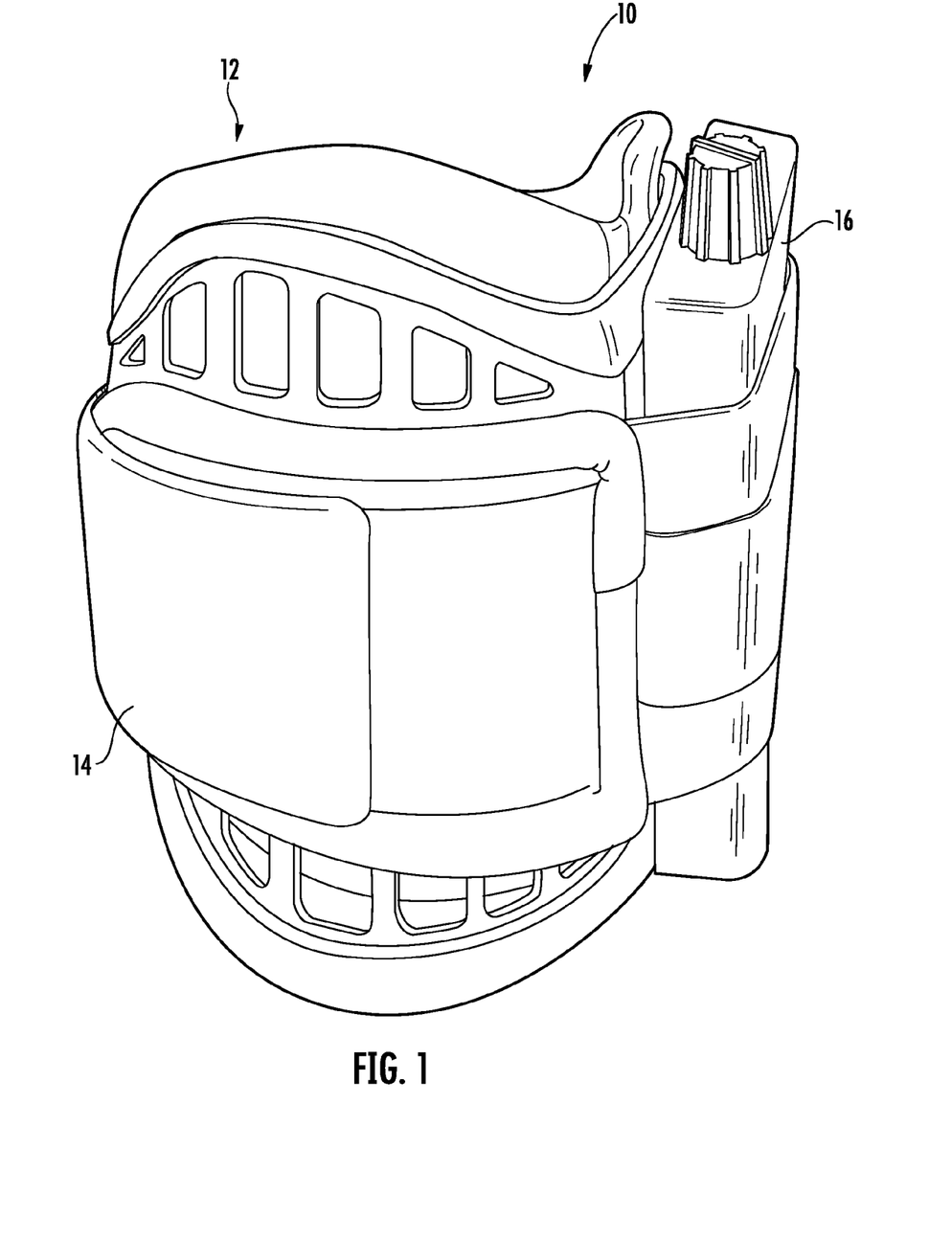
FIG. 1 is a front perspective view of a cuff assembly according to an exemplary embodiment.
Figure 2:
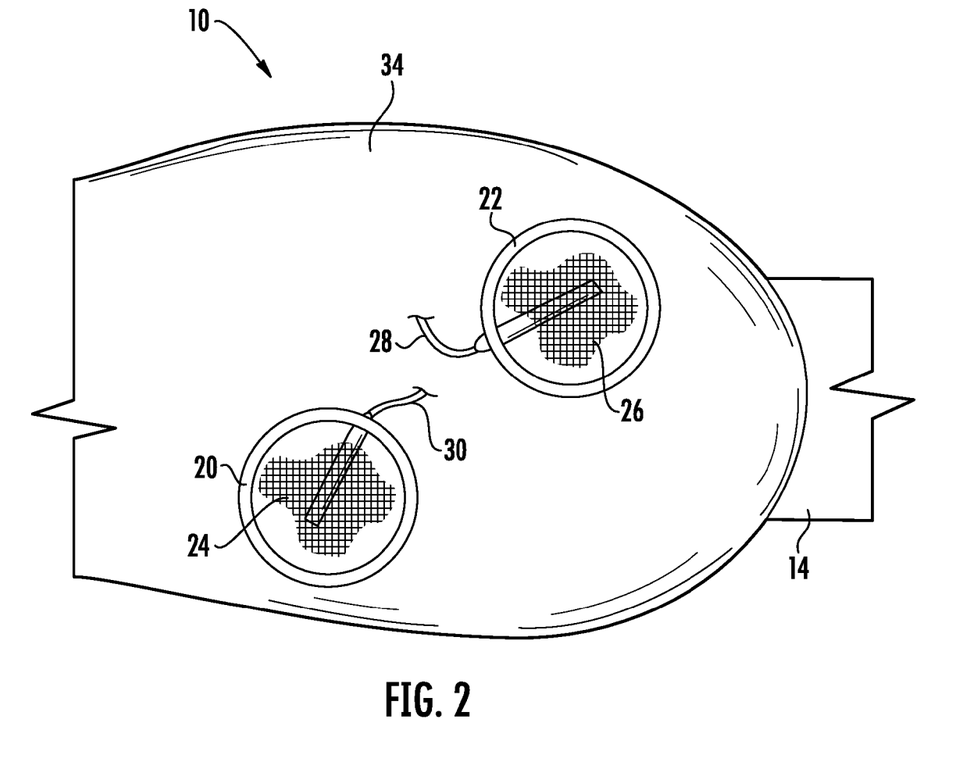
FIG. 2 is a perspective view of a portion of an interior of a cuff assembly according to an exemplary embodiment
Figure 3:
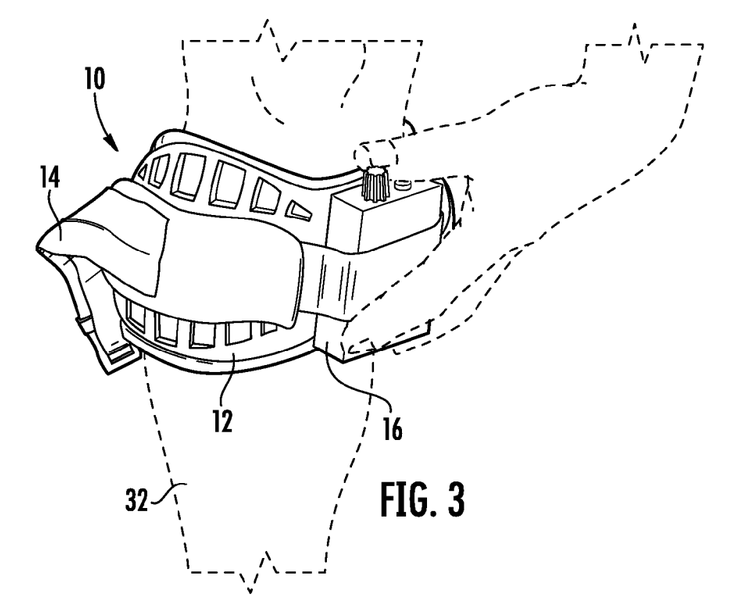
FIG. 3 is a front view of a cuff assembly positioned on a limb of a user according to an exemplary embodiment.
Figure 4:
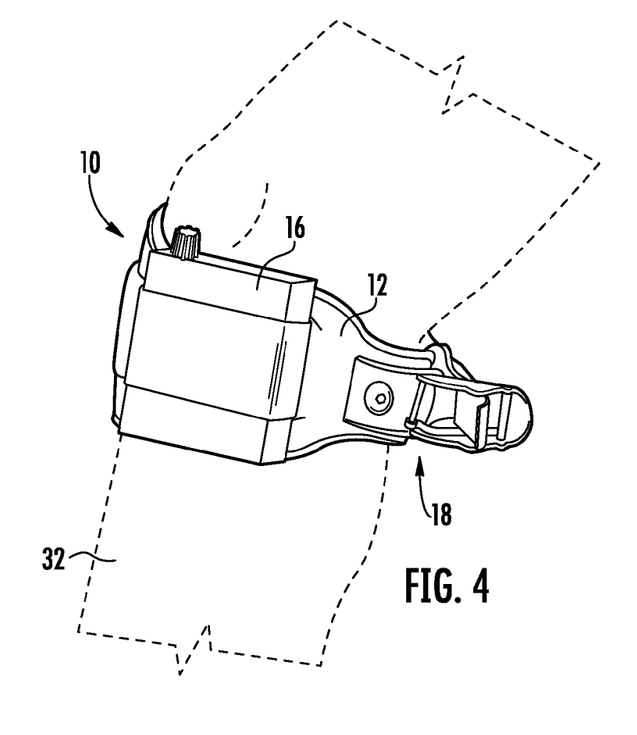
FIG. 4 is a side view of a cuff assembly positioned on a limb of a user according to an exemplary embodiment.
Figure 12:
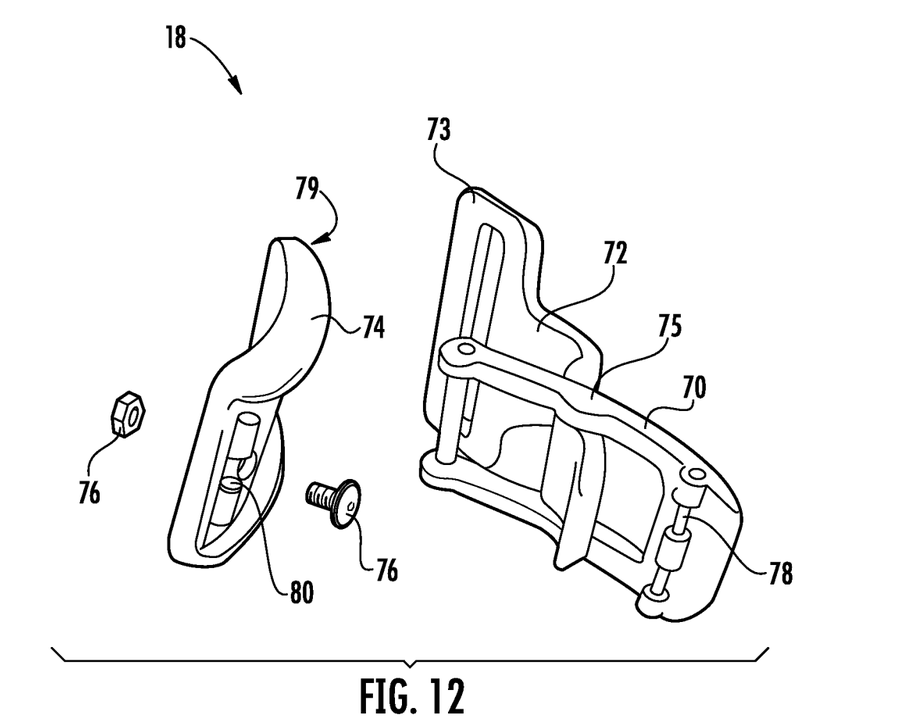
FIG. 12 is an exploded view of a closure device according to an exemplary embodiment.

Referring now to FIGS. 4-5 and 12, closure mechanism 18 (e.g., an over center latch, closure mechanism, buckle, closure device, etc.) will be described in greater detail according to an exemplary embodiment. As shown in FIG. 12, closure mechanism 18 includes a base 74, a first clip member 72 (e.g., a band, etc.), and a second clip member 70 (e.g., an over center clip, a rotating clip, etc.). According to an exemplary embodiment, base 74 is coupled to frame assembly 12 via one or more fastening members 76 (e.g., screws, nuts, adhesive members, hook and loop fasteners, etc.). In one embodiment, base 74 is rotatably coupled to frame assembly 12 to permit a limited amount of pivoting of base 74 relative to frame assembly 12 and to facilitate closing of closure mechanism 18. One portion 73 of first clip member 72 is coupled to one end of strap 14 (e.g., end 82 of strap 14 shown in FIG. 13) and a second portion of first clip member 72 is pivotally coupled to second clip member 70 via a pivot 75 (e.g., via a pin extending through apertures in both first and second clips 72, 70).

Referring further to FIG. 12, second clip 70 includes a pin member 78 (e.g., an extension, etc.) configured to be received within recesses 80 (e.g., notches, etc.) provided in base 74 when closure mechanism 18 is fully closed. In one embodiment, pin member 78 is slightly oversized relative to recess 80 to provide a snap fit interface between the components.

When closure mechanism 18 is in an open position, clip members 70, 72 may be physically separated from base 74 so as to permit removal of cuff 10 from limb 32 in a lateral direction (e.g., eliminating the need to pull cuff 10 up and/or down over the foot to don/doff the assembly). In order to close closure mechanism 18, pivot member 77 is first placed into a corresponding recess 79 in base 74. A user may then rotate second clip 70 about pivot member 77 until pin member 78 is securely received within recesses 80 in a snap fit fashion. As second clip 70 is rotated, first clip 72 is likewise moved circumferentially about frame assembly 12, thereby decreasing the circumference of frame assembly 12 and increasing the compressive force applied to limb 32. This increase in compressive force ensures that cuff 10 remains in place during physical activity of the use and ensures electrode contact with the skin.

In some embodiments, closure mechanism 18 is an over center closure device, such that the force required to rotate second clip 70 increases (e.g., from a fully open position) as second clip 70 is rotated, reaches a maximum at approximately the center point of rotation (e.g., at the "over center" location), and then decreases as second clip 70 is rotated further toward the fully closed position. According to one embodiment, the maximum force required to close closure mechanism 18 is 5 pounds. According to alternate embodiments, the maximum force required to close closure mechanism 18 may be more or less than 5 pounds (e.g., 2 pounds, 3 pounds, 7 pounds, etc.).

It should be noted that closure mechanism 18 can be easily opened and closed by a user through the use of only a single hand. This may be beneficial in situations where a user experiencing problems with, for example, a left leg, is also experiencing problems with the left hand. For example, such problems often arise in connection with stroke victims, people suffering from multiple sclerosis (MS), and from a variety of other medical conditions. In some embodiments, closure mechanism 18 may be located to a medial side of limb 32 (e.g., along an inside portion) to facilitate opposite single-hand manipulation of closure mechanism 18 (as shown, e.g., in FIGS. 3-4).

Figure 13:
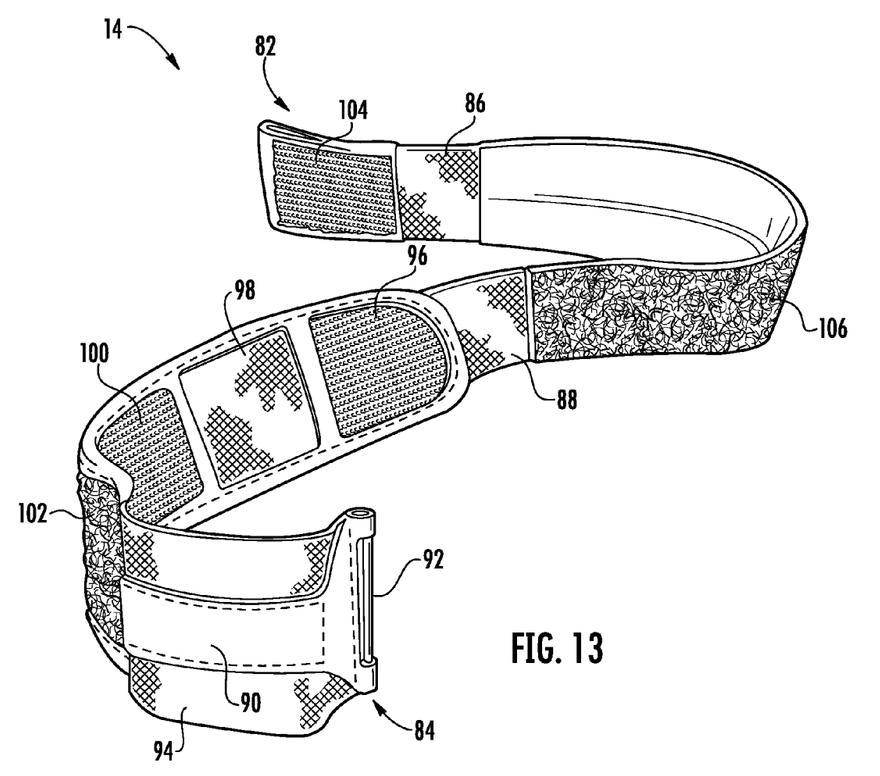
FIG. 13 is a perspective view of a strap assembly to be used with a cuff assembly according to an exemplary embodiment.

Referring now to FIG. 13, strap assembly 14 is shown in greater detail according to an exemplary embodiment. Generally, strap 14 extends about all or a portion of frame assembly 12 when cuff 10 is in use. As shown in FIG. 13, strap assembly 14 includes a first end 82 and a second end 84. First end 82 may include a loop configured to be coupled to a portion of closure mechanism 18 (e.g., first clip member 72 shown in FIG. 12), and second end 84 may include a pin member 92 configured to be received in pin retainer 48 on frame assembly 12 (see, e.g., FIGS. 6 and 8). Strap 14 may include one or more portions 86, 88 that comprises an elastic material configured to provide cuff 10 with a degree of mechanical compliance relative to limb 32 to permit for physical activity, muscle flexion, etc. For example, portions 86, 88 allow the cuff circumference to expand and contract with leg circumferential changes during walking to keep cuff 10 from moving axially along the leg. Strap assembly 14 may further include one or more pads 96-106 on either side of strap assembly 14 that include a hook and/or loop material and are usable to couple various components of cuff 10 to strap 14. Further, one or more of pads 96-106 may be usable to conceal wires 28, 30 that extend from control unit 16 to electrode assemblies 24, 26. For example, according to one embodiment, pad 98 may form a pocket or recess that is configured to receive one or more of wires 28, 30, thereby reducing the chance that wires 28, 30 will snag on other components during use of cuff 10. Further yet, one or more of pads 96-106 may be provided with a length-adjustment feature so as to allow a user to adjust the length of strap 14.

Referring further to FIG. 13, strap assembly 14 includes a control unit cover 94 and a reinforcement member 90. When strap assembly 14 extends about frame assembly 12, cover 94 and frame assembly 12 may form a recess, or pocket, which receives control unit 16. Cover 94 may be open on both ends so that control unit 16 may be inserted from either a top or bottom position. Reinforcement member 90 may be made from a different material (e.g., a polyester, etc.) from the remainder of strap assembly 14. Further, cover 94 may be at least partially elastic so as to securely retain control unit 16 during use, and may be configured to provide user access to the battery compartment and connector(s) of control unit 16. Various portions of strap assembly 14 may be latex-free elastic, polyester, and/or nylon material to avoid irritation of the users skin.

Figure 14:
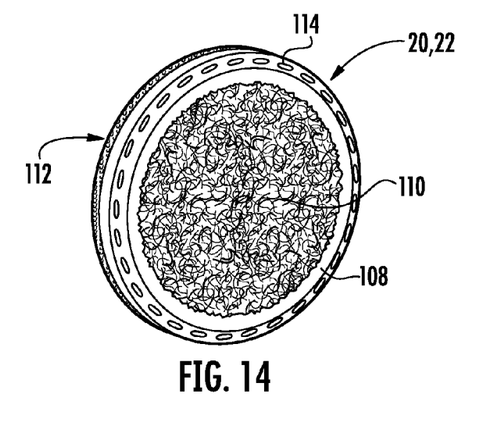
FIG. 14 a perspective view of an electrode locator according to an exemplary embodiment.

Referring now to FIG. 14, electrode locators 20, 22 are shown in greater detail. Electrode locators 20, 22 are used to facilitate proper placement of electrode assemblies 24, 26 relative to limb 32. Locators 20, 22 include a generally circular ring 108 (e.g., a silicone ring), an inner surface 110, and an outer surface 112. Inner and outer surfaces 110, 112 may comprise hook and/or loop material to facilitate securing outer surface 112 of locators 20, 22 to liner assembly 34 and to facilitate securing inner surface 110 of locators 20, 22 to electrode assemblies 24, 26 (see, e.g., FIG. 2). According to an exemplary embodiment, locators 20, 22 each include a thread material 114 that extends about the perimeter of locators 20, 22. A different color material (e.g., one black, and one read) may be used for each of locators 20, 22. While locators 20, 22 are shown as generally circular in shape, any desired shape may be used (e.g., square, rectangular, etc.). In some embodiments, locators 20, 22 are circular and have a diameter of approximately 1.25 inches, although according to various alternative embodiments, locators 20, 22 may have a variety of different diameters (e.g., approximately 1.88 inches, more or less than 1.25 inches, etc.).

During an initial wearing of cuff 10, the positions of electrode assemblies 24, 26 may be varied using a trial and error type calibration procedure to determine the best placement of the electrodes. Once the proper placement of the electrodes is determined, electrode assemblies 24, 26 may be fastened to electrode locators 20, 22, which are in turn fastened to liner assembly 34. Various combinations of hook and loop fasteners may be used to coupled electrode locators 20, 22 to electrode assemblies 24, 26 and/or liner assembly 34.

Figure 15:
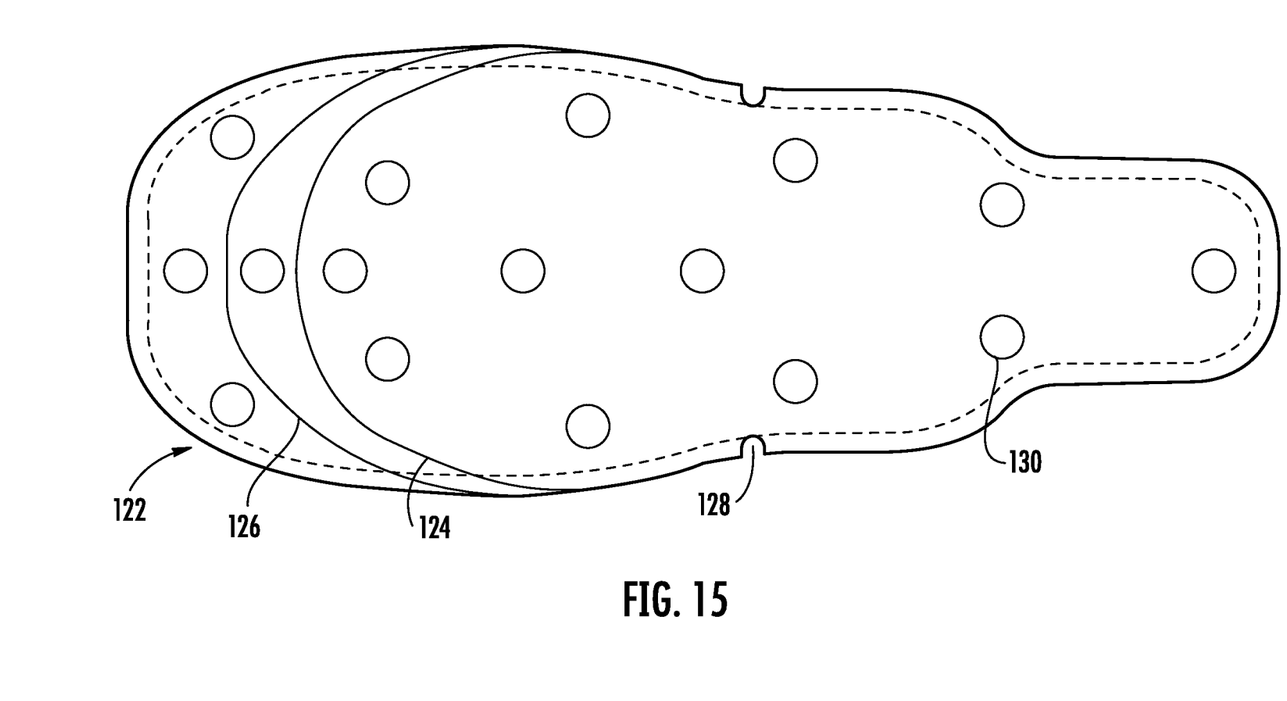
FIG. 15 is a plan view of a disposable liner according to an exemplary embodiment.

Referring now to FIG. 15, a disposable liner 122 is shown according to an exemplary embodiment. As shown in FIG. 15, disposable liner 122 may be a generally planar piece of material (e.g., a fabric, paper, etc.) having a shape similar to liner assembly 34. Liner 122 may be provided with imprinted cut lines 124, 126 or other suitable markings identifying where liner 122 may be cut to fit varying sizes of cuffs (e.g., for large (as shown), medium (cut line 126), and small (cut line 124)). Liner 122 may include a notch 128 or other suitable marking that aligns with the tibial crest of a user and tibial crest locator 36 on liner assembly 34. The outer surface of liner 122 (e.g., the surface facing away from a limb) may include one or more pads 130 provided with hook and loop material and/or adhesive features that enable a user to temporarily secure liner 122 to the inner surface of liner assembly 34. The inner surface of liner 122 (e.g., the surface facing a limb) may also include a hook and/or loop material and may receive locators 20, 22 and/or electrodes 24, 26 as discussed above.

Disposable liner 122 may facilitate the use of cuff 10 with a variety of different users (e.g., as part of a physical therapist's treatment) such that a number of users may use a single cuff assembly. Each different user may be allocated a separate disposable liner 122, which may be inserted and removed from liner assembly 34 as appropriate. Liner 122 may be provided with a writable surface such that the locations of locators 20, 22 may be marked directly onto the liner to indicate where locators 20, 22 should be positioned. Further, liner 122 may be marked with patient information such as identification information, medical information, etc.

Figure 18:
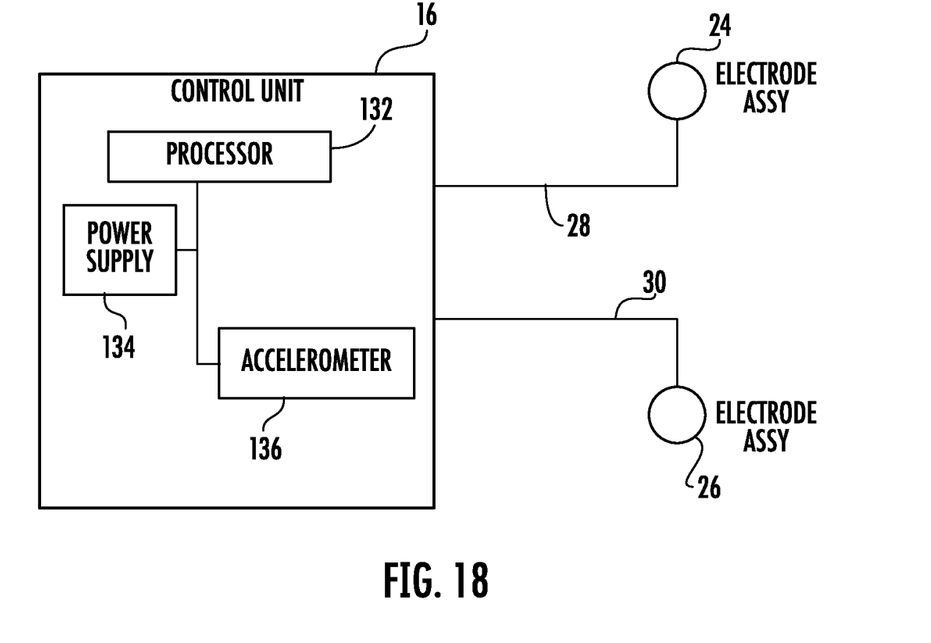
FIG. 18 is a general block diagram of a functional electrical stimulation system according to an exemplary embodiment.

Cuff assembly 10 may be used in connection with a variety of medical devices, including a variety of FES systems that may restore neuro-muscular functionality to patients. Referring to FIG. 18, a block diagram of an FES system is shown according to an exemplary embodiment. In one embodiment, control unit 16 may be electrically coupled to electrode assemblies 24, 26 via wires 28, 30. Control unit 16 controls the electrical signals sent to electrode assemblies 24, 26. In one embodiment, control unit 16 includes a processor 132, a power supply 134, and an accelerometer 136. Based on signals received from accelerometer 136, processor 132 may determine the tilt angle of a user's leg (e.g., the angle between the lower leg, or shank, and a level surface), and may provide electrical signals to electrode assemblies 24, 26 at appropriate times (e.g., to determine a start/stop stimulation pattern or timing sequence during walking to avoid dragging of the foot and toes). In some embodiments, control unit 16 is provided on the medial side of the tibial crest, which is a generally flat, boney area, without excessive flesh such that cuff 10 and control unit 16 tend to move less in this area relative to other areas of the leg. The compressive force provided by closure mechanism 18 serves to both properly locate control unit 16 and to ensure proper contact between the electrodes and the skin, which in turn ensures proper electrical stimulation of the nerve(s) and/or muscle(s) of the user. According to various other embodiments, cuff 10 may be used with other control units that may operate in similar or different ways.

It should be noted that the cuff assembly described in connection with the various exemplary embodiments provided herein may provide many benefits to users. For example, the construction and arrangement of the frame assembly and the closure mechanism facilitate one-handed attachment and removal of the cuff from a user's leg. Further, when initially placed on the leg, the flexible or resilient construction of the cuff assembly resists sliding and/or other movement relative to a user's leg. Further yet, the cuff may accommodate different-sized legs, and may be reversible such that it may be used on either a left or right leg by flipping the assembly upside down. For example, various components of the cuff assembly (e.g., the frame assembly, strap assembly, etc.) may be generally symmetrical about a line of symmetry extending along the length of the cuff, such that be flipping the cuff assembly upside down the cuff may be fitted to an opposite leg.

The cuff also provides an effective support for a control module and/or one or more electrodes, by providing a secure attachment mechanism for the control module and locators that facilitate consistent and proper locating of the electrodes with each don and doff of the cuff assembly. Further, the cuff provides a compressive force perpendicular to a user's skin, thereby ensuring proper contact between the electrodes and the skin. To avoid skin irritation, various components of the cuff may be made of a latex-free and/or hypoallergenic material that is breathable. Further yet, to facilitate attachment and removal of the cuff, portions of the frame assembly may be provided with varying levels of flexibility to provide a clamping force around a user's leg. For example, the skeleton frame member may be formed in multiple stages, utilizing materials of differing harness (e.g., differing durometer values, differing flexibility or rigidity, etc.) in a series of injection molding processes where layers of polymer material are over-molded together to form a composite skeleton having multiple hardness characteristics.

It is important to note that the construction and arrangement of the elements of the cuff assembly as shown in the exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the embodiments. For example, for purposes of this disclosure, the term "coupled" shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to mechanical, fluid, or electrical relationship between the two components. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. A cuff assembly comprising:
   a frame assembly configured to be positioned about a lower leg of a user and support a functional electrical stimulation system, wherein the lower leg has a tibial crest; and
   an over center closure mechanism coupled to the frame assembly and configured to secure the frame assembly relative to the limb, the over center closure mechanism being located on a medial side of the limb when the frame assembly is positioned about the lower leg, wherein the over center closure mechanism includes:
   a first clip member having an opening configured to receive a strap coupled to the frame assembly, a second clip member having a first pin and a second pin, wherein the first clip member is pivotally coupled to the second clip member through the first pin, and a base member having a recess, wherein the base member is coupled to the frame assembly, and wherein the recess is configured to removably and pivotally receive the second pin such that the second clip member can pivot with respect to the base member;

wherein the frame assembly is symmetric about a line of symmetry extending along a length of the frame assembly, and wherein the over center closure mechanism is positioned along the line of symmetry.

2. The cuff assembly of claim 1, wherein at least a portion of the frame assembly comprises a flexible material, wherein the over center closure mechanism is moveable from an open position to a closed position to increase a compressive force applied by the frame assembly to the lower leg, and wherein the frame assembly is configured to remain in a desired position on the lower leg when the frame assembly is positioned about lower leg limb and the over center closure mechanism is in the open position.

3. The cuff assembly of claim 2, wherein the over center closure mechanism is a low profile latch providing for a snap fit when the over center closure mechanism is in the closed position.

4. The cuff assembly of claim 1, wherein the over center closure mechanism is moveable from the open position to the closed position by moving a latch member toward the tibial crest of the user.

5. The cuff assembly of claim 1, wherein the frame assembly extends substantially around the lower leg and defines a gap between two ends of the frame assembly, wherein a strap extends about at least a portion of a circumference of the frame assembly and over the gap, and wherein at least one end of the strap is coupled to the over center closure mechanism.

6. The cuff assembly of claim 5, wherein one end of the strap is coupled to the over center closure mechanism and a second end of the strap is coupled to the frame assembly.

7. The cuff assembly of claim 1, wherein the over center closure mechanism comprises an injection molded material.

8. The cuff assembly of claim 1, wherein the over center closure mechanism is configured to be moveable between the open position and the closed position via single-handed manipulation by the user.

9. The cuff assembly of claim 1, wherein the frame assembly is usable in a first configuration on a left leg and in a second configuration on a right leg, wherein the over center closure mechanism is located to the medial side of the limb in both the first and second configurations.

10. The cuff assembly of claim 1, wherein the frame assembly includes a skeleton member formed of a first material and a second material, wherein the first material is more flexible than the second material.

11. The cuff assembly of claim 10, wherein the second material is over-molded onto at least a portion of the first material.

12. A cuff assembly comprising:
a frame assembly having a length and configured to be positioned about a lower leg of a user and support a functional electrical stimulation system; and
an over center closure mechanism coupled to the frame assembly and configured to secure the frame assembly relative to the lower leg, the over center closure mechanism being located on a medial side of the limb when the frame assembly is positioned about the lower leg, wherein the over center closure mechanism includes:
a first clip member having an opening configured to receive a strap coupled to the frame assembly,
a second clip member having a first pin and a second pin, wherein the first clip member is pivotally coupled to the second clip member through the first pin, and
a base member having a recess, wherein the base member is coupled to the frame assembly, and wherein the recess is configured to romovably and pivotally receive the second pin such that the second clip member can pivot with respect to the base member;
wherein the frame assembly comprises an outer periphery defined by a top peripheral portion and a bottom peripheral portion, the top peripheral portion being symmetric to the bottom peripheral portion along the length of the frame assembly and about a longitudinal axis of the frame assembly.

13. The cuff assembly of claim 12, wherein the frame assembly is configured such that the relative positions of the top and bottom peripheral portions are reversible to enable the cuff assembly to be worn on either leg with the over center closure mechanism being located on the medial side of the a lower leg.

14. The cuff assembly of claim 12, wherein the top peripheral portion comprises at least one first curved portion and at least one first straight portion, and wherein the bottom peripheral portion comprises at least one second curved portion and at least one second straight portion, the first and second straight portions being generally parallel along a portion of the length of the frame assembly.

15. The cuff assembly of claim 14, wherein the first curved portion and the second curved portion are convex relative to and symmetric about the longitudinal axis of the frame assembly.

16. A medical support device, comprising:
a flexible assembly configured to be positioned about a leg of a user and configured to support a functional electrical stimulation system having a control unit on an outside surface of the flexible assembly and an electrode on an inside surface of the flexible assembly; and
a closure mechanism coupled to the flexible assembly and configured to secure the flexible assembly relative to the limb, wherein the closure mechanism is located on a medial side of the limb when the frame assembly is positioned about the leg, wherein the closure mechanism includes:
a first clip member having an opening configured to receive a strap coupled to the flexible assembly,
a second clip member having a first pin and a second pin, wherein the first clip member is pivotally coupled to the second clip member through the first pin, and
a base member having a recess, wherein the base member is coupled to the flexible assembly, and wherein the recess is configured to removably and pivotally receive the second pin such that the second clip member can pivot with respect to the base member;
wherein the electrode is controlled by the control unit via a wire that runs through the flexible assembly; and
wherein the flexible assembly is symmetric about a line of symmetry extending along a length of the flexible assembly, and wherein the closure mechanism is positioned along the line of symmetry.

\* \* \* \* \*